United States Patent
Dacquay et al.

(10) Patent No.: US 9,022,970 B2
(45) Date of Patent: *May 5, 2015

(54) OPHTHALMIC INJECTION DEVICE INCLUDING DOSAGE CONTROL DEVICE

(75) Inventors: Bruno Dacquay, Irvine, CA (US); Casey Lind, Irvine, CA (US); Cesario Dos Santos, Aliso Viejo, CA (US); Robert J Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 738 days.

This patent is subject to a terminal disclaimer.

(21) Appl. No.: 12/444,044

(22) PCT Filed: Oct. 9, 2007

(86) PCT No.: PCT/US2007/080756

§ 371 (c)(1), (2), (4) Date: Apr. 2, 2009

(87) PCT Pub. No.: WO2008/115270

PCT Pub. Date: Sep. 25, 2008

(65) Prior Publication Data

US 2010/0030136 A1 Feb. 4, 2010

Related U.S. Application Data

(63) Continuation-in-part of application No. 11/688,573, filed on Mar. 20, 2007, now Pat. No. 7,811,252.

(60) Provisional application No. 60/921,497, filed on Oct. 16, 2006, provisional application No. 60/921,498, filed on Oct. 16, 2006, provisional application No. 60/921,499, filed on Oct. 16, 2006.

(51) Int. Cl.
*A61M 5/315* (2006.01)
*A61F 9/00* (2006.01)
(Continued)

(52) U.S. Cl.
CPC .......... *A61F 9/0017* (2013.01); *A61M 5/14224* (2013.01); *A61M 5/20* (2013.01);
(Continued)

(58) Field of Classification Search
CPC . A61M 5/20; A61M 5/1452; A61M 5/31525; A61M 2210/0612
USPC ............... 604/31, 151, 152, 154, 155, 890.1
See application file for complete search history.

(56) References Cited

U.S. PATENT DOCUMENTS

| 1,252,614 A | 1/1918 | Pieper |
| 3,089,815 A | 5/1963 | Lieb et al. |

(Continued)

FOREIGN PATENT DOCUMENTS

| AU | 7623298 | 6/1998 |
| CA | 1313802 | 2/1993 |

(Continued)

OTHER PUBLICATIONS

European Patent Office, European Search Report, Application No. 07874450.5, Publication No. 2077810, Published Jul. 15, 2009, 7 pages.

(Continued)

*Primary Examiner* — Nathan R Price

(74) *Attorney, Agent, or Firm* — Kenneth D. Bassinger

(57) ABSTRACT

An injection device includes a dispensing chamber, a plunger, a controller, a temperature control device, and a memory device. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is fluidly sealed to the inner surface of the dispensing chamber. The controller controls the operation of the injection device. The temperature control device at least partially surrounds the dispensing chamber. The memory device has a parameter stored on it. The controller uses the parameter from the memory device to operate the injection device.

6 Claims, 6 Drawing Sheets

(51) Int. Cl.
*A61M 5/142* (2006.01)
*A61M 5/20* (2006.01)

(52) U.S. Cl.
CPC ....... *A61M 5/31525* (2013.01); *A61M 5/31546* (2013.01); *A61M 2205/0244* (2013.01); *A61M 2205/3368* (2013.01); *A61M 2205/3606* (2013.01); *A61M 2205/3653* (2013.01); *A61M 2205/6018* (2013.01); *A61M 2210/0612* (2013.01)

(56) References Cited

U.S. PATENT DOCUMENTS

| | | |
|---|---|---|
| 3,199,740 A | 8/1965 | Huffa et al. |
| 3,608,549 A | 9/1971 | Merrill |
| 3,858,581 A | 1/1975 | Kamen |
| 3,892,537 A | 7/1975 | Gulati et al. |
| 3,982,537 A | 9/1976 | Bucalo |
| 4,007,742 A | 2/1977 | Banko |
| 4,030,499 A | 6/1977 | Bucalo |
| 4,054,138 A | 10/1977 | Bucalo |
| 4,122,850 A | 10/1978 | Bucalo |
| 4,184,510 A | 1/1980 | Murry et al. |
| 4,246,932 A | 1/1981 | Raines |
| 4,265,618 A | 5/1981 | Herskovitz et al. |
| 4,357,136 A | 11/1982 | Herskovitz et al. |
| 4,392,827 A | 7/1983 | Martin |
| 4,474,752 A | 10/1984 | Haslam et al. |
| 4,484,915 A | 11/1984 | Tartaglia |
| 4,582,488 A | 4/1986 | Newman |
| 4,684,344 A | 8/1987 | Brockway et al. |
| 4,704,088 A | 11/1987 | Newman |
| 4,713,446 A | 12/1987 | DeVore et al. |
| 4,764,165 A | 8/1988 | Reimels et al. |
| 4,795,423 A | 1/1989 | Osterholm |
| 4,830,855 A | 5/1989 | Stewart |
| 4,911,161 A | 3/1990 | Schechter |
| 4,992,045 A | 2/1991 | Beisel |
| 5,066,276 A | 11/1991 | Wang |
| 5,120,307 A | 6/1992 | Wang |
| 5,328,481 A | 7/1994 | Wang |
| 5,336,175 A | 8/1994 | Mames |
| 5,360,413 A | 11/1994 | Leason et al. |
| 5,370,630 A | 12/1994 | Smidebush et al. |
| 5,431,630 A | 7/1995 | Leonard |
| 5,476,511 A | 12/1995 | Gwon et al. |
| 5,487,725 A | 1/1996 | Peyman |
| 5,503,144 A | 4/1996 | Bacon |
| 5,582,595 A | 12/1996 | Haber et al. |
| 5,602,188 A | 2/1997 | Nakanishi |
| 5,620,700 A | 4/1997 | Berggren et al. |
| 5,662,612 A | 9/1997 | Niehoff |
| 5,743,886 A | 4/1998 | Lynn et al. |
| 5,773,019 A | 6/1998 | Ashton et al. |
| 5,783,205 A | 7/1998 | Berggren et al. |
| 5,824,072 A | 10/1998 | Wong |
| 5,860,949 A | 1/1999 | Chen |
| 5,882,338 A | 3/1999 | Gray |
| 5,925,022 A * | 7/1999 | Battiato et al. ................. 604/208 |
| 5,928,197 A | 7/1999 | Niehoff |
| 5,928,663 A | 7/1999 | Peyman |
| 5,958,080 A | 9/1999 | Kang |
| 5,984,889 A | 11/1999 | Christ et al. |
| 6,051,011 A | 4/2000 | Weidenbenner |
| 6,076,013 A * | 6/2000 | Brennan et al. ................. 607/2 |
| 6,165,190 A | 12/2000 | Nguyen |
| 6,210,357 B1 | 4/2001 | Morris |
| 6,221,045 B1 | 4/2001 | Duchon et al. |
| 6,270,343 B1 | 8/2001 | Martin |
| 6,290,690 B1 | 9/2001 | Huculak et al. |
| 6,311,868 B1 | 11/2001 | Krietemeier et al. |
| 6,364,865 B1 | 4/2002 | Lavi et al. |
| 6,372,245 B1 | 4/2002 | Bowman et al. |
| 6,413,245 B1 | 7/2002 | Yaacobi et al. |
| 6,419,656 B1 | 7/2002 | Vetter et al. |
| 6,436,143 B1 | 8/2002 | Ross et al. |
| 6,488,659 B1 | 12/2002 | Rosenman |
| 6,520,930 B2 | 2/2003 | Critchlow et al. |
| 6,585,700 B1 | 7/2003 | Trocki et al. |
| 6,595,979 B1 | 7/2003 | Epstein et al. |
| 6,620,189 B1 | 9/2003 | Machoold et al. |
| 6,635,267 B1 | 10/2003 | Miyoshi et al. |
| 6,645,179 B1 | 11/2003 | Ishikawa et al. |
| 6,726,654 B2 | 4/2004 | Rosenman |
| 6,940,209 B2 | 9/2005 | Henderson |
| 6,991,457 B2 | 1/2006 | Kazen et al. |
| 7,176,030 B2 | 2/2007 | Faries, Jr. et al. |
| 2002/0055720 A1 | 5/2002 | Hohlfelder et al. |
| 2003/0055380 A1 | 3/2003 | Flaherty |
| 2003/0125665 A1 | 7/2003 | Rosenman |
| 2003/0231990 A1 | 12/2003 | Faries, Jr. et al. |
| 2004/0039253 A1 | 2/2004 | Peyman et al. |
| 2004/0052761 A1 | 3/2004 | Vernon et al. |
| 2004/0054319 A1 | 3/2004 | Langley et al. |
| 2004/0133155 A1 | 7/2004 | Varner et al. |
| 2004/0167466 A1 | 8/2004 | Drasler et al. |
| 2004/0176720 A1 | 9/2004 | Kipfer |
| 2004/0204673 A1 | 10/2004 | Flaherty |
| 2004/0210200 A1 | 10/2004 | Gerondale et al. |
| 2004/0231667 A1 | 11/2004 | Horton et al. |
| 2005/0065477 A1 | 3/2005 | Jost |
| 2006/0047250 A1 | 3/2006 | Hickingbotham |
| 2007/0016186 A1 | 1/2007 | LoRusso |
| 2007/0060887 A1 * | 3/2007 | Marsh et al. ................. 604/113 |
| 2007/0142769 A1 | 6/2007 | Griffiths et al. |
| 2007/0270750 A1 | 11/2007 | Dacquay et al. |
| 2009/0069806 A1 | 3/2009 | De La Mora Levy et al. |

FOREIGN PATENT DOCUMENTS

| | | |
|---|---|---|
| DE | 3434930 A1 | 4/1986 |
| EP | 0 516 292 | 2/1922 |
| EP | 0348146 A1 | 6/1989 |
| EP | 0356372 A2 | 2/1990 |
| EP | 0398394 | 11/1990 |
| EP | 1516638 | 3/2005 |
| EP | 1704840 A1 | 9/2006 |
| GB | 1551767 | 5/1979 |
| JP | 2002/059055 A | 2/2002 |
| RU | 2270032 C2 | 2/2006 |
| SU | 285170 | 10/1970 |
| WO | WO 82/03761 | 11/1982 |
| WO | WO 87/00029 | 1/1987 |
| WO | WO 93/11818 | 6/1993 |
| WO | WO 96/03978 | 2/1996 |
| WO | WO 99/33853 | 7/1999 |
| WO | WO 99/52575 A1 | 10/1999 |
| WO | WO 99/65548 | 12/1999 |
| WO | WO 00/74752 A1 | 12/2000 |
| WO | WO 01/10482 A1 | 2/2001 |
| WO | WO 02/07658 A1 | 1/2002 |
| WO | WO 03/006098 | 1/2003 |
| WO | WO 2006/037969 | 4/2006 |
| WO | WO 2006/050008 A1 | 5/2006 |
| WO | WO 2006/067480 | 6/2006 |
| WO | WO 2006/108026 A2 | 10/2006 |
| WO | WO 2008/115270 A2 | 9/2008 |
| WO | WO 2008/115270 A3 | 4/2009 |

OTHER PUBLICATIONS

International Searching Authority, International Searching Report and Written Opinion of the International Searching Authority, PCT/US2007/080756, Nov. 18, 2008, 6 pages.

Inozemtsev, V.A., "Study of Element Base of Digital Equipment," Chapter 1.8 "Storage Device," Fig. 1.65, Bryansk, BGU Publisher, 2002.

* cited by examiner

OPHTHALMIC INJECTION DEVICE INCLUDING DOSAGE CONTROL DEVICE

RELATED APPLICATIONS

This Application is a continuation-in-part of U.S. patent application Ser. No. 11/688,573 filed Mar. 20, 2007 and U.S. patent application Ser. No. 11/435,906 filed May 17, 2006, and claims the benefit of U.S. Patent Application No. 60/921,497 filed Oct. 16, 2006, U.S. Patent Application No. 60/921,498 filed Oct. 16, 2006 and U.S. Patent Application No. 60/921,499 filed Oct. 16, 2006. This Application is also a US National Stage under 35 U.S.C. 371 of PCT/US2007/080756 filed Oct. 9, 2007.

BACKGROUND OF THE INVENTION

The present invention relates to a device for injecting a drug into an eye and more particularly to an ophthalmic drug delivery device with a dosage control mechanism and methods of operating the system.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to pierce the eye tissue with the needle, hold the syringe steady, and actuate the syringe plunger (with or without the help of a nurse) to inject the fluid into the eye. Fluid flow rates are uncontrolled. The volume injected is typically not controlled in an accurate manner because reading the vernier is subject to parallax error. Tissue damage may occur due to an "unsteady" injection.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. With this type of dispenser, the volumes delivered are highly dependent on fluid viscosity, surface tension, and the specific dispensing tip. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. While precise, this dispenser is expensive and requires an electrical signal to be delivered to the dispensing mechanism.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a dosage control device for an ophthalmic injection system that assures that the correct dosage is delivered during each injection. Such a device would eliminate dosing error on the part of medical professionals during an injection and would be desirable for insuring accurate dosing during a clinical trial of a drug.

SUMMARY OF THE INVENTION

In one embodiment consistent with the principles of the present invention, the present invention is an injection device having a dispensing chamber, a plunger, a controller, a temperature control device, and a memory device. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is fluidly sealed to the inner surface of the dispensing chamber. The controller controls the operation of the injection device. The temperature control device at least partially surrounds the dispensing chamber. The memory device has parameters stored on it. The controller uses the parameters from the memory device to operate the injection device.

In another embodiment consistent with the principles of the present invention, the present invention is a method of injecting a substance into an eye comprising: recognizing a connection between a tip segment and a limited reuse assembly; reading parameters from a memory device in the tip segment; operating the limited reuse assembly and tip segment based on the parameters to deliver a substance into an eye.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 2:
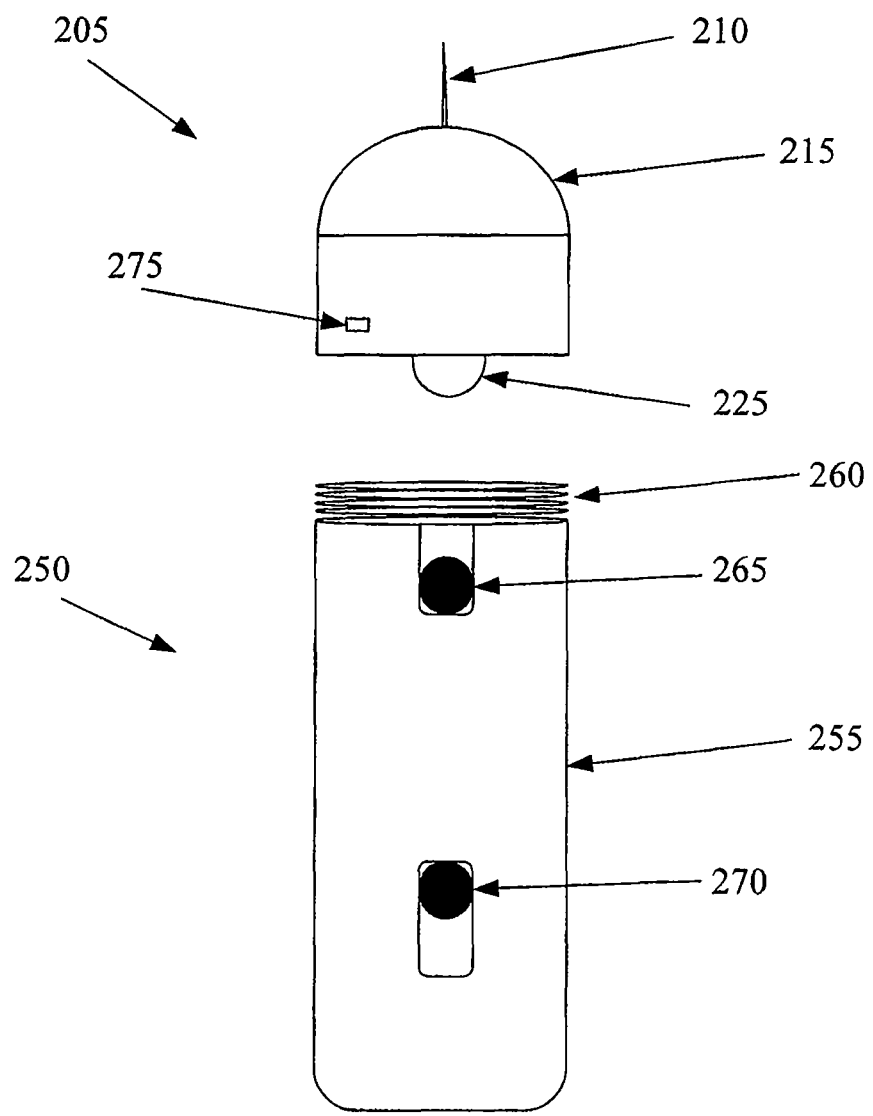
FIG. 2 is a view of an ophthalmic hand piece including a drug delivery tip segment and a limited reuse assembly according to an embodiment of the present invention.

FIG. 2 depicts one view of an ophthalmic hand piece including a drug delivery tip segment and a limited reuse assembly according to an embodiment of the present invention. In FIG. 2, the hand piece includes a tip segment 205 and a limited reuse assembly 250. The tip segment 205 includes a needle 210, a housing 215, a plunger connection 225, and an optional light 275. The limited reuse assembly 250 includes a housing 255, a switch 270, a lock mechanism 265, and a threaded portion 260.

Tip segment 205 is capable of being connected to and removed from Limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of the tip segment. For example, optional light 275 may also pulse on and off to indicate other states such as but not limited to a system error, fully charged battery, insufficiently charged battery or faulty connection between the tip segment 205 and limited use assembly 250.

Figure 3:
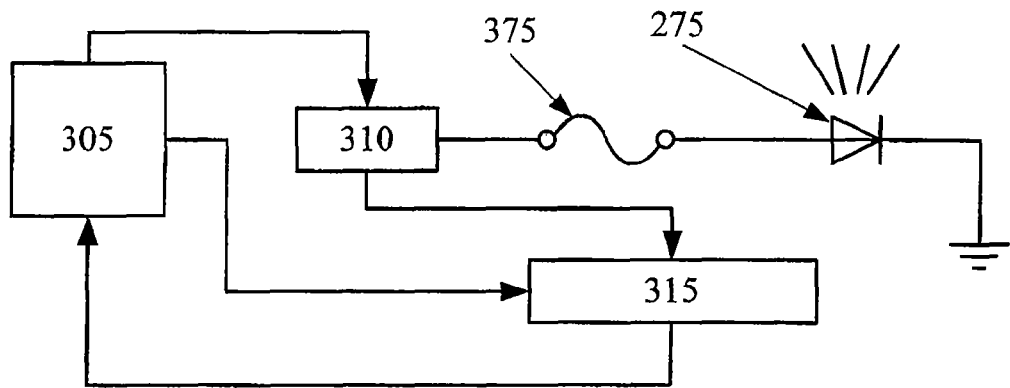
FIG. 3 is a diagram of a memory device circuit for use in a drug delivery tip segment according to an embodiment of the present invention.

FIG. 3 is a diagram of a memory device circuit for use in a drug delivery tip segment according to an embodiment of the present invention. In FIG. 3, the circuit includes optional light 275, fuse 375, controller 305, power source 310, and memory device 315. Controller 305 controls the operation of power source 310 and reads data stored on memory device 315.

In the embodiment of FIG. 3, optional light 275 is a light emitting diode of any appropriate color. In other embodiments, optional light 275 may be a lamp, a phosphorescent light, or any other similar electric or electronic light source. In other embodiments, optional light 275 is any type of indicator, such as a liquid crystal display or a segmented display.

Fuse 375 is a fuse with a current rating greater than the operating current of optional light 275. Fuse 375 may be a common glass encapsulated fuse, a trace fuse on a printed circuit board, or other similar structure that provides the function of a fuse. For example, a switch or switching circuit may be used to provide the functionality of fuse 375. Fuse 375 may be blown after use to prevent reuse of the tip segment.

Power source 310 is typically a rechargeable battery with associated electronics. In other cases, power source 310 is a disposable battery or simply a connection to an independent power source, such as a switch mode power supply. In this embodiment, power source 310 also includes the charging and current driving electronics associated with it.

Figure 1:
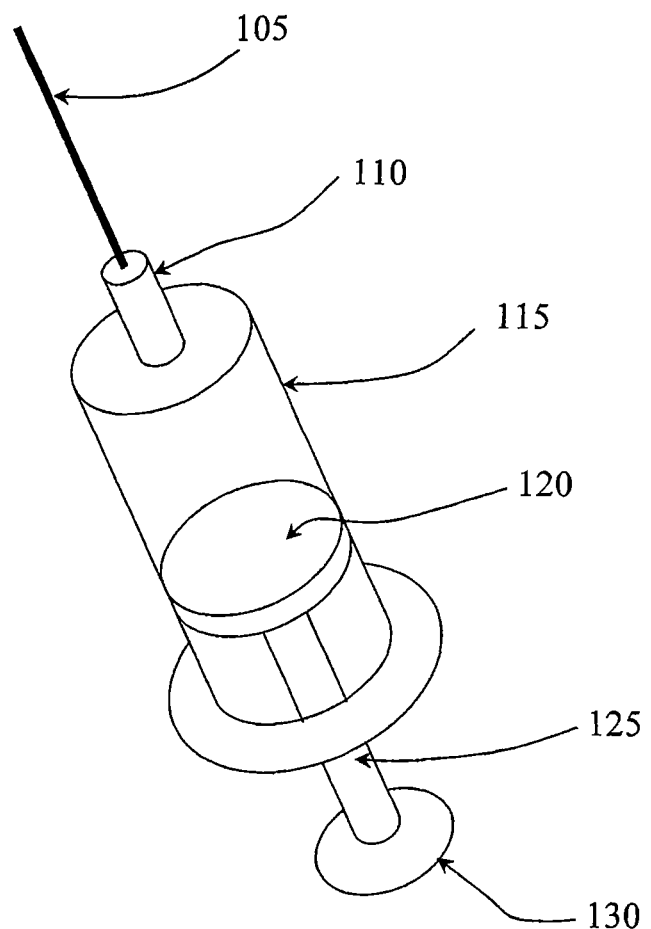
FIG. 1 is a perspective view of a prior art syringe.

Controller 305 is typically an integrated circuit with power, input, and output pins capable of performing logic functions. In various embodiments, controller 305 is a targeted device controller. In such a case, controller 305 performs specific control functions targeted to a specific device or component, such as a heater or a power supply. For example, a heater controller has the basic functionality to control a heater. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. In the embodiment of FIG. 3, controller 305 controls power supply 310 and reads data from memory device 315. While depicted as one component in FIG. 1, controller 305 may be made of many different components or integrated circuits.

Figure 8:
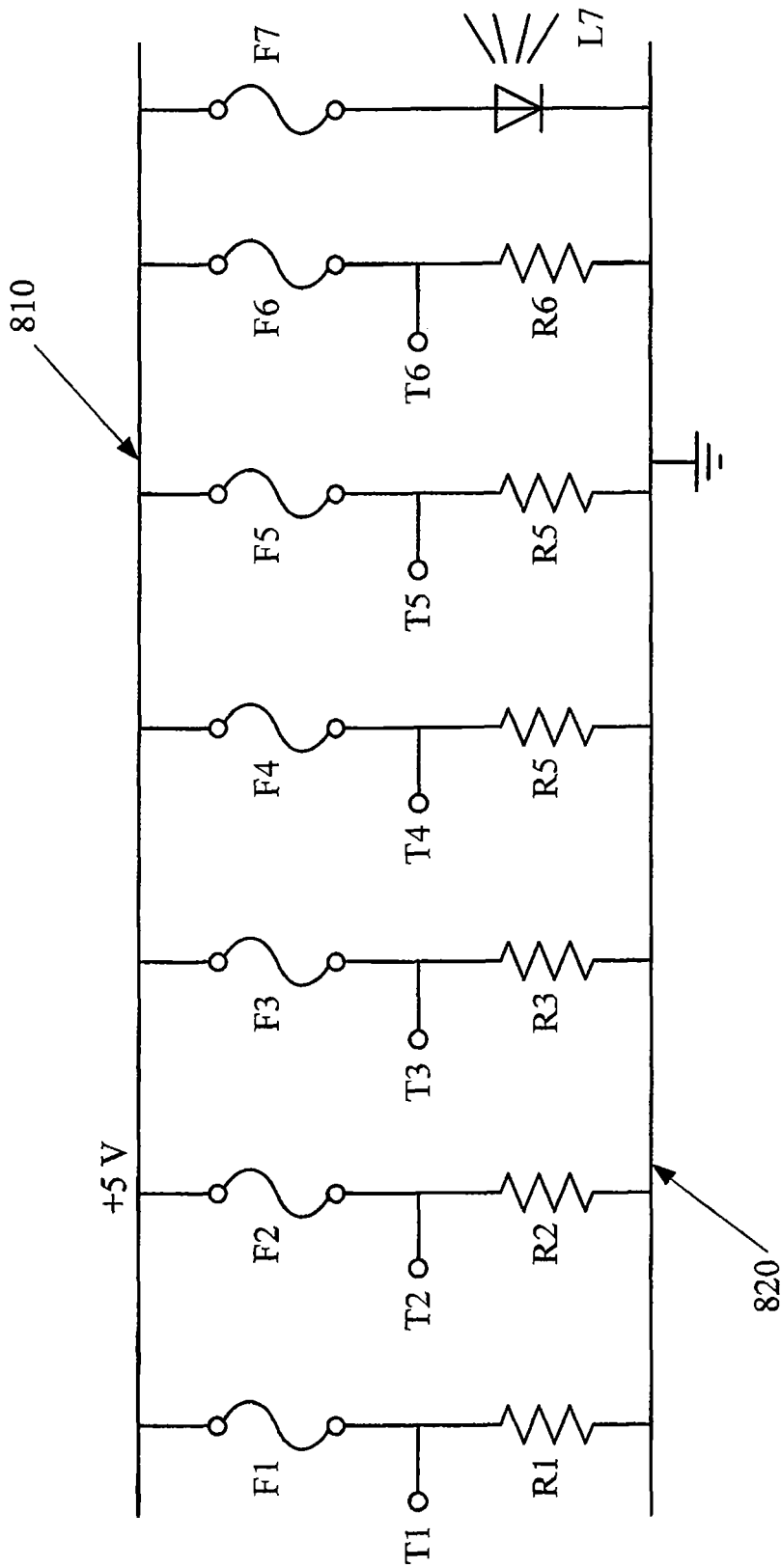
FIG. 8 is a circuit diagram of a hard-wired memory circuit according to an embodiment of the present invention.

Memory device 315 is a hard wired memory device such as that described in FIG. 8. Unlike a typical semiconductor memory, such as an EEPROM or flash memory, which cannot withstand gamma sterilization without data loss, memory device 315 withstands gamma sterilization without data loss. Memory device 315 is typically packaged with a disposable tip segment or drug delivery device. Such a package is sterilized before leaving the factory. In order to preserve the data stored on memory device 315, memory device 315 is hard-wired or resistant to commonly used sterilization techniques, such as gamma sterilization.

Figure 4:
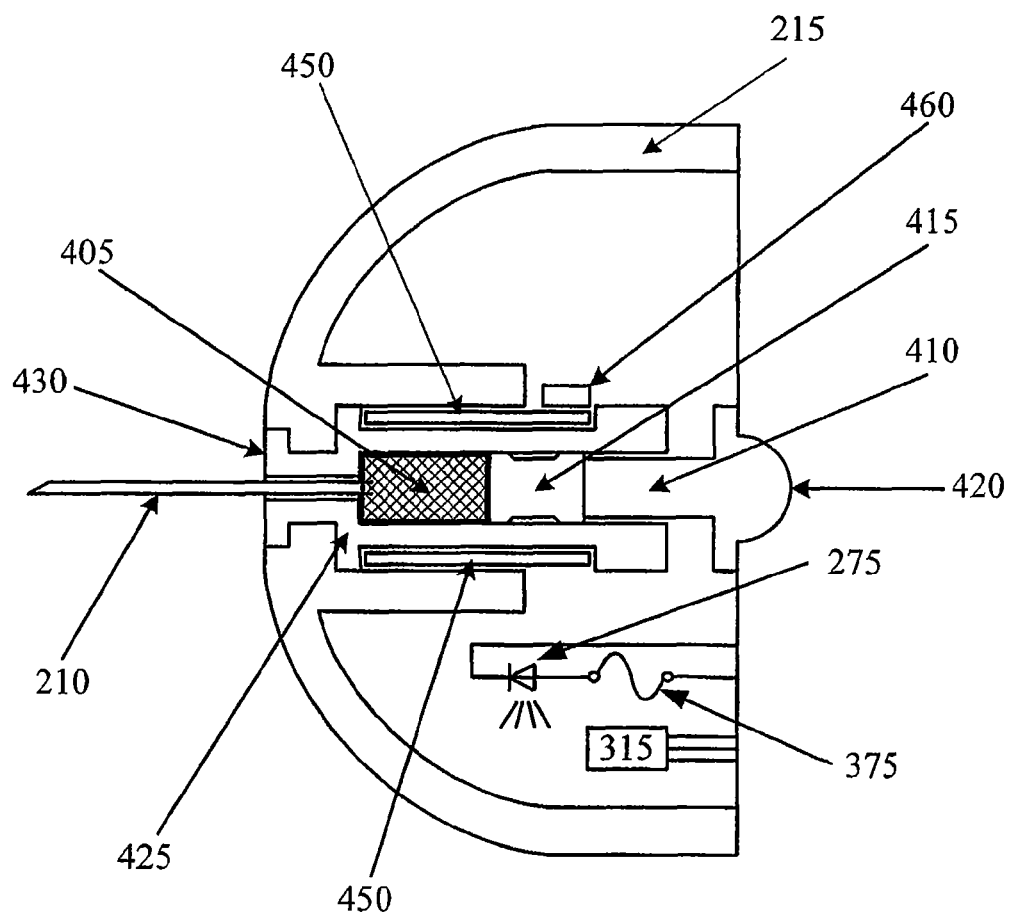
FIG. 4 is an exploded cross section view of a drug delivery tip segment for an ophthalmic hand piece according to an embodiment of the present invention.

FIG. 4 is an exploded cross section view of a drug delivery tip segment for an ophthalmic hand piece according to an embodiment of the present invention. In FIG. 4, the drug delivery tip segment includes housing 215, needle 210, optional light 275, fuse 375, memory device 315, plunger shaft 410, plunger tip (or fluid seal) 415, mechanical linkage interface 420, dispensing chamber 405, dispensing chamber housing 425, temperature control device 450, thermal sensor 460, and optional luer 430.

In the embodiment of FIG. 4, mechanical linkage interface is located on one end of plunger shaft 410. Plunger tip 415 is located on the other end of plunger shaft 410. Plunger shaft 410 and plunger tip 415 collectively form a plunger. Dispensing chamber 405 is enclosed by dispensing chamber housing 425 and plunger tip 415. Plunger tip 415 forms a fluid seal with the interior surface of dispensing chamber housing 425. Needle 210 is fluidly coupled to dispensing chamber 405. In this manner, a substance located in dispensing chamber 405 can be contacted by plunger tip 415 and pushed out of needle 210. Needle 210 may be secured to the drug delivery tip segment by an optional luer 430 or may be permanently attached. Temperature control device 450 is located on dispensing chamber housing 425 and at least partially surrounds dispensing chamber 405. Housing 215 forms an outer skin on the drug delivery tip segment and at least partially encloses plunger shaft 410, plunger tip 415, dispensing chamber 405, and dispensing chamber housing 425.

A substance to be delivered into an eye, typically a drug, is located in dispensing chamber 405. In this manner, the substance is contacted by the inner surface of dispensing chamber housing 425 and one face of plunger tip 415. Typically, dispensing chamber 405 is cylindrical in shape. Temperature control device 450 is in thermal contact with dispensing chamber housing 425. In this manner, temperature control device 450 is adapted to heat and/or cool the contents of dispensing chamber 425. Current is applied to temperature control device 450 through an electrical interface (not shown). Thermal sensor 460 provides temperature information to assist in controlling the operation of temperature control device 450.

In one embodiment of the present invention, the substance located in dispensing chamber 405 is a drug that is preloaded into the dispensing chamber. In such a case, the drug delivery tip segment is appropriate as a single use consumable product. Such a disposable product can be assembled at a factory with a dosage of a drug installed. A precise volume of a substance can be preloaded into the delivery device.

When the drug is preloaded into dispensing chamber 405, a set quantity of the drug can be preloaded. For example, 100 microliters of a drug can be loaded into dispensing chamber 405, and any quantity up to 100 microliters can be dispensed. In such a case, the plunger (plunger shaft 410 and plunger tip 415) can be moved a precise distance to deliver a precise dosage of drug from the dispensing chamber 405, through the needle 210, and into an eye. This provides for flexibility of dosing and for ease of assembly.

In other embodiments, different dosages may be preloaded into different tip segments. For example, dosages up to ten microliters in one microliter increments may be preloaded into dispensing chamber 405 of different tip segments. The proper dosage may be selected by selecting the tip segment with the proper amount of drug preloaded in dispensing chamber 405.

In operation, the drug delivery tip segment of FIG. 4 is attached to a limited reuse assembly (not shown). The limited reuse assembly provides power to the tip segment and illuminates optional light 275. In such a case, a current passes through optional light 275 and fuse 375. Mechanical linkage interface 420 mates with a mechanical interface on the limited reuse assembly. Dosage information such as drug type, dosage volume, operating temperature, injection speed, thermal expansion coefficient, density and other information may be read from memory device 315. This dosage information enables the controller to operate the plunger such that the correct dosage is delivered. When a force is applied to plunger shaft 410, plunger tip 415 is displaced. The displacement of plunger tip 415 in turn displaces the substance contained in dispensing chamber 405. The substance is pushed out of needle 210. After the dosage is delivered, the controller (not shown) directs an increased current to be sent through fuse 375. This increased current burns out fuse 375 indicating that the tip segment has been used and is to be discarded. Since the tip segment of the depicted embodiment is a single use tip segment, once fuse 375 is blown, the tip segment is no longer operable. In addition, once fuse 375 is blown, data cannot be read from memory device 315.

Figure 5:
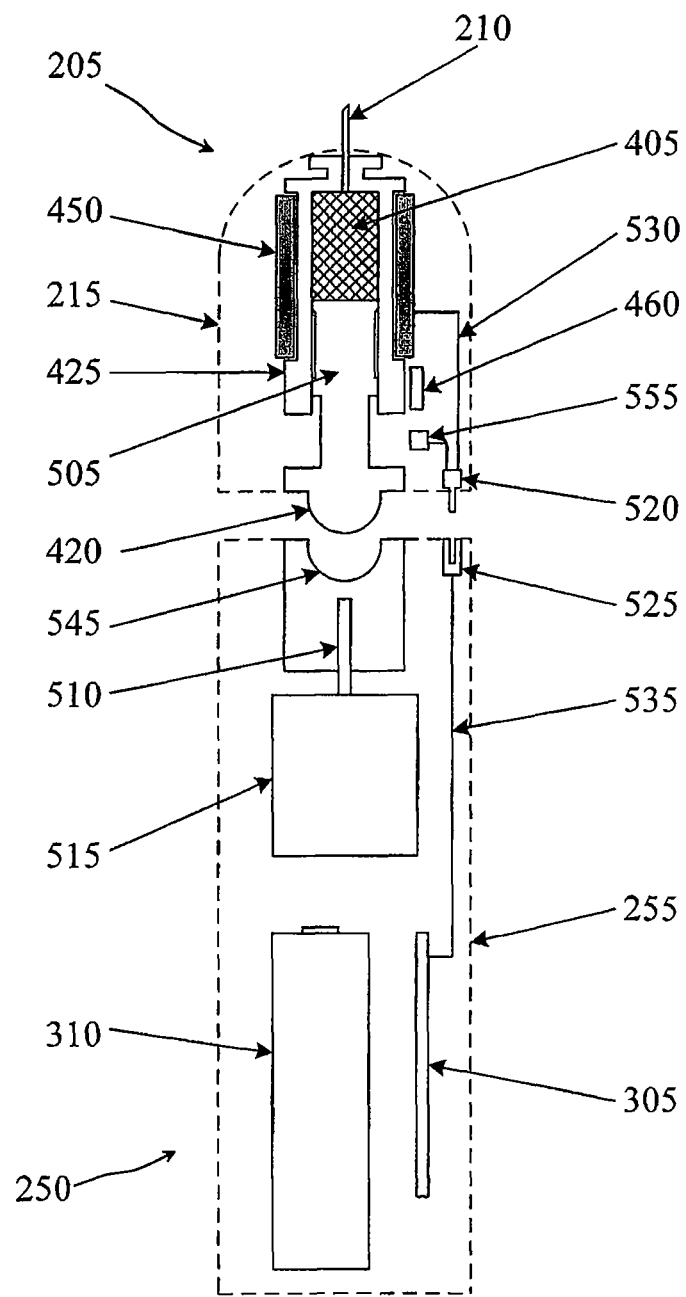
FIG. 5 is a cross sectional view of a drug delivery tip segment and a limited reuse assembly according to an embodiment of the present invention.

FIG. 5 is a cross section view of a drug delivery tip segment and a limited reuse assembly according to an embodiment of the present invention. FIG. 5 shows how tip segment 205 interfaces with limited reuse assembly 250. In the embodiment of FIG. 5, tip segment 205 includes memory assembly 555, mechanical linkage interface 420, plunger 505, dispensing chamber housing 425, tip segment housing 215, temperature control device 450, thermal sensor 460, needle 210, dispensing chamber 405, interface 530, and tip interface connector 520. Limited reuse assembly 250 includes mechanical linkage 545, actuator shaft 510, actuator 515, power source 310, controller 305, limited reuse assembly housing 255, interface 535, and limited reuse assembly interface connector 525.

In tip segment 205, mechanical linkage 420 is located on one end of plunger 505. The other end of plunger 505 forms one end of dispensing chamber 405. Plunger 505 is adapted to slide within dispensing chamber 405. An outer surface of plunger 505 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. In this case, temperature control device 450 is adapted to heat and/or cool dispensing chamber housing 425 and any substance contained in dispensing chamber 405. In other words, temperature control device 450 is in thermal contact with dispensing chamber housing 425. Interface 530 connects temperature control device 450 with tip interface connector 520.

The components of tip segment 205, including dispensing chamber housing 425, temperature control device 450, and plunger 505 are at least partially enclosed by tip segment housing 215. In one embodiment consistent with the principles of the present invention, a seal is present on a bottom surface of tip segment housing 215. In this manner, plunger 505 is sealed to tip segment housing 215. This seal prevents contamination of any substance contained in dispensing chamber 405. For medical purposes, such a seal is desirable. This seal can be located at any point on plunger 505 or on dispensing chamber housing 425. In such a case, tip segment housing 215 maybe connected to dispensing chamber housing 425 to form an air tight or fluid tight seal. In another embodiment, tip segment housing 215 maybe sealed to plunger 505 near the end on which mechanical linkage interface 420 resides. In such a case, an air tight or fluid tight seal may be formed between a location on plunger 505 and tip segment housing 215.

In addition, tip segment 205 may contain a plunger stop mechanism. As shown in FIG. 5, the bottom portion of plunger 505 (the portion on which mechanical linkage interface 420 resides) is adapted to contact the bottom portion of dispensing chamber housing 425. In such a case, as plunger 505 advances upward toward needle 210, mechanical linkage interface 420 also advances upward toward needle 210. A top surface of mechanical linkage interface 420 contacts a bottom surface of dispensing chamber housing 425. In this embodiment, the protrusions on the bottom end on plunger 505 and the bottom surface of dispensing chamber housing 425 form a plunger stop mechanism. Plunger 505 cannot be advanced any further than the point at which the top surface of mechanical linkage interface 420 contacts the bottom surface of dispensing chamber housing 505. Such a plunger stop mechanism can provide a safety feature, such as to prevent plunger 505 from contacting needle 210 and possibly dislodging it. In another embodiment consistent with the principles of the present invention, such a plunger stop mechanism may also include a locking mechanism so that plunger 505 cannot be retracted or moved away from needle 210 when needle 210 is removed from the eye. Such a plunger lock mechanism helps to prevent reflux of the substance when needle 210 is removed.

In limited reuse assembly 250, power source 310 provides power to actuator 515. An interface (not shown) via the controller 305 connects the power source 310 to the actuator 515. Actuator 515 is connected to actuator shaft 510. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210 mechanical linkage 545 also moves upward toward needle 210.

Controller 305 is connected via interface 535 to limited reuse assembly interface connecter 525. Limited reuse assembly interface connecter 525 is located on a top surface of limited reuse assembly housing 255 adjacent to mechanical linkage interface 545. In this manner, both limited reuse assembly interface connector 525 and mechanical linkage interface 545 are adapted to be connected with tip interface connector 520 and mechanical linkage interface 420 respectively.

Controller 305 and actuator 515 are connected by an interface (not shown). This interface (not shown) allows controller 305 to control the operation of actuator 515. Controller 305 has the ability to interface with either a rechargeable or non rechargeable power source 310. Controller 305 may control the current or voltage provided to memory assembly 555, for example, to illuminate an optional light 275 and or blow a fuse 375 contained within memory assembly 555.

Tip segment 205 is adapted to mate with or attach to limited reuse assembly 250 as previously described. In the embodiment of FIG. 5, mechanical linkage interface 420 located on a bottom surface of plunger 505 is adapted to connect with mechanical linkage interface 545 located near a top surface of limited reuse assembly housing 255. In addition, tip interface connector 520 is adapted to connect with limited reuse assembly interface connector 525. When tip segment 205 is connected to limited reuse assembly 250 in this manner, actuator 515 and actuator shaft 510 are adapted to drive plunger 505 upward toward needle 210. In addition, an interface is formed between controller 305 and temperature control device 450. A signal can pass from controller 305 to temperature control device 450 through interface 535, limited reuse assembly interface connector 525, tip interface connector 520, and interface 530.

In operation, when tip segment 205 is connected to limited reuse assembly 250, controller 305 controls the operation of actuator 515. Actuator 515 is actuated and actuator shaft 510 is moved upward toward needle 210. In turn, mechanical linkage interface 545, which is connected to mechanical linkage interface 420, moves plunger 505 upward toward needle 210. A substance located in dispensing chamber 405 is then expelled through needle 210.

In addition, controller 305 controls the operation of temperature control device 450. Temperature control device 450 is adapted to heat and/or cool an outside surface of dispensing chamber housing 425. Since dispensing chamber housing 425 is at least partially thermally conductive, heating dispensing chamber housing 425 heats a substance located in dispensing chamber 405. Temperature information can be transferred from thermal sensor 460 through interface 530, tip interface connector 520, limited reuse assembly interface connector 525, and interface 535 back to controller 305. This temperature information can be used to control the operation of temperature control device 450. Typically, controller 305 controls the amount of current that is sent to temperature control device 450. When temperature control device 450 is a heater, the more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

Memory assembly 555 is connected to interface 530 in tip segment 205. In the present embodiment, memory assembly 555 includes optional light 275, fuse 375, and memory device 315 as described with respect to FIGS. 3 and 4. The memory device 315 in memory assembly 555 is typically a hard wired memory circuit like that depicted in FIG. 8. The memory device 315 in memory assembly 555 is configured to store dosage information for a drug contained in dispensing chamber 405.

Controller 305 is also adapted to interface with memory assembly 555. In this manner, controller 305 directs current to flow from power source 310 to memory assembly 555. Controller 305 also reads data from the memory device contained in memory assembly 555. A current passing through optional light 275 and fuse 375 illuminates optional light 275. After the tip segment 205 has been used (after the substance has been dispensed), controller 305 directs power source 310 to deliver an increased current to blow fuse 375 and extinguish optional light 275. This indicates that the tip segment 205 has been used and that it should be discarded. In addition, controller 305 may check fuse 375 to see if it is blown. If it is blown, controller 305 defines tip segment 205 as rendered inoperable. Alternatively, fuse 375 may be placed such that when it is blown, no power is delivered to the tip segment. In such a case, once fuse 375 is blown, optional light 275 is extinguished and the tip segment is rendered inoperable. In addition, once fuse 375 is blown, data may no longer be read from the memory device in memory assembly 555.

In the embodiment of FIG. 5, interface 530, tip interface connector 520, limited reuse assembly interface 525, and interface 535 all form a data interface between tip segment 205 and limited reuse assembly 250. In this manner, information from the thermal sensor 460 maybe passed back to limited reuse assembly 250 via this series of interfaces and interface connectors. In addition, data stored on the memory device in memory assembly 555 may also be read by controller 305 via this series of interfaces and interface connectors. When tip segment 205 is connected to limited reuse assembly 250, mechanical linkage interface 545 is connected to mechanical linkage interface 420 and tip interface connector 520 is connected to limited reuse assembly interface connector 525. The connection of tip interface connector 520 to limited reuse assembly interface connector 525 allows the transfer of information or data from thermal sensor 460 and the memory device in memory assembly 555 to controller 305.

In one embodiment consistent with the principle of the present invention, the memory device in memory assembly 555 stores drug type, dosage volume, operating temperature, injection speed, thermal expansion coefficient, density and other information. Information about the drug contained in dispensing chamber 405 is stored in the memory device in memory assembly 555. In such a case, controller 305 can read the drug information from the memory device in memory assembly 555 and control the operating temperature, injection rate and injection volume in a manner suitable to deliver the proper drug dosage and potentially identify to the use the type of drug loaded for delivery. For example, 100 microliters may be contained in dispensing chamber 405. Information stating that a dosage of 20 microliters is to be delivered into an eye, heated to 70 C., and has a thermal expansion coefficient of 1.10 maybe stored on the memory device in memory assembly 555. In such a case, controller 305 reads the drug information (that 20 microliters should be delivered into the eye, that the operating temperature is 70 C., and that the thermal expansion coefficient is 1.10) from the memory device in memory assembly 555. Controller 305 can then operate temperature control device 450 to heat the drug to 70 C. and operate actuator 515 to deliver the 20 microliter dosage. Controller 305 can cause actuator 515 to move actuator shaft 510 and mechanical linkage 545 a set distance related to a dosage of 20 microliters and the thermal expansion coefficient of 1.10. In such a case, plunger 505 is moved this set distance so that only 20 micro liters of a drug is expelled from needle 210 and into an eye.

In one embodiment consistent with the principles of the present invention, controller 305 has various plunger distances stored on it along with the operating temperature, thermal expansion coefficient, drug type and other pertinent information. Each of these plunger distances is related to a different dosage. For example, one plunger distance may be associated with a dosage of 20 microliters and a second larger plunger distance may be associated with a dosage of 40 microliters. In this manner controller 305 can use the set plunger distance to control actuator 515, actuator shaft 510, mechanical linkage interface 545, and mechanical linkage interface 420 to move plunger 505 this set distance. In other words, controller 305 reads dosage information from the memory device in memory assembly 555, finds the plunger distance associated with that dosage, and uses the distance that plunger 505 must travel to deliver a given dosage of drug. Since actuator shaft 510 and mechanical linkage interface 545 are connected to mechanical linkage interface 420, a movement of actuator shaft 510 produces a corresponding movement of plunger 505. When actuator 515 is a stepper motor, controller 305 controls the movement of actuator 515 such that plunger 505 is moved the proper distance to deliver the required dosage from dispensing chamber 405, through needle 210, and into an eye.

In another embodiment consistent with the principles of the present invention, controller 305 may calculate a distance that plunger 505 must be moved to deliver the desired dosage. For example, if dosage information corresponding to a drug dosage of 20 microliters is read from the memory device along with the operating temperature and the thermal expansion coefficient in memory assembly 555 by controller 305, then controller 305 may use this information to calculate a proper distance that plunger 505 must be moved. Since the volume of dispensing chamber 405 as well as the volume of a drug loaded in dispensing chamber 405 is known, a distance that plunger 505 must be moved to deliver that required dosage can be calculated by controller 305. When dispensing chamber 405 has a cylindrical shape, the volume of the dispensing chamber can be calculated by using the cross section area of the cylinder (the area of a circle) times the height of the dispensing chamber. This simple mathematical formula can be used to calculate the total volume of the dispensing chamber 405. Since the cross section area of dispensing chamber 405 is constant for any given application, the height which corresponds to a distance that plunger 505 travels can be calculated for any dosage amount.

For example, assume that 100 mg of drug when heated to a given operating temperature expands by 1.1 (thermal coefficient of expansion) to yield 100 microliters of a drug, is loaded into dispensing chamber 405 and that the cross section area of dispensing chamber 405 is 10. When dispensing chamber 405 is in the shape of a cylinder, the height of that cylinder is also 10. To deliver a dosage of 20 microliters which corresponds to 20% of the total volume of dispensing chamber 405, it is necessary to move plunger 505 upward toward needle 210 a distance of 2. In other words, a dosage of 20 microliters corresponds to 20% of the total volume of dispensing chamber 405 after the drug has expanded. In such a case, plunger 505 should be moved upward toward needle 210 a distance equal to 20% of the total height of dispensing chamber 405. Controller 305 can then control actuator 515 such that actuator shaft 510 drives plunger 505 upward a distance of 20% of the total height of dispensing chamber 405.

In addition, controller 305 may read information about a rate at which plunger 505 should be moved in order to properly deliver a dosage of drug. In such a case, controller 305 reads information about the rate of drug delivery from memory assembly 555 and uses that information to operate actuator 515 to drive plunger 505 at that rate. The rate at which plunger 505 moves may be fixed or variable. In some applications, it may be desirable to move plunger 505 faster than in other applications. For example, when the drug contained in dispensing 405 is a drug that should be heated before being injected into an eye, it maybe desirable to drive plunger 505 at a rate such that the heated drug does not cool and clog needle 210. In other applications, it may be desirable to move plunger 505 slowly in order to improve the delivery of a drug contained in dispensing chamber 405.

It is also desirable to include dosage information on the memory device in memory assembly 555 so that a dosing error is less likely to occur. In such a case, a number of different drug delivery tip segments 205 maybe manufactured and loaded with a drug at the factory. Dosage information can also be loaded onto the memory device in memory assembly 555 at the factory. A number of different tip segments, each with the same amount of drug contained in the dispensing chamber 405 but with different dosage information stored on the memory device in memory assembly 555, can be manufactured and shipped. Alternatively, a number of different tip segments, each with a different amount of drug contained in the dispensing chamber 405 with corresponding dosage information stored on the memory device in memory assembly 555, can be manufactured and shipped. A doctor can then order the tip segment 205 with the required dosage information on the memory device in memory assembly 555. Packaging can be clearly labeled to identify the dosage information so that the proper dosage is administered to a patient. Where memory assembly 555 is located on a separate card 600, that card 600 can be included with the drug delivery device 405.

In other embodiments of the present invention, memory device 555 contains information about the characteristics of the tip segment and/or the drug itself. For example, memory device 555 may contain a drug identifier. Such an identifier can be used to properly identify the drug contained in the tip segment. When a number of different drugs are contained in a number of different tip segments, a drug identifier can be useful in determining the type of drug in a particular tip segment. The drug identifier can be paired with information on the best mode of delivering the drug. For example, when a drug is suspended in a phase transition compound, the drug identifier can include information about the best way to deliver the drug. This additional information can include dosage information, delivery rate information, thermal expansion coefficient and temperature control information. For example, it may be desirable to deliver the drug and phase transition compound at a fixed rate after it reaches a fixed temperature. In such a case, information stored on memory device 555 can serve as inputs to controller 305 to optimally control the delivery of the drug.

In such a manner, a set of optimal delivery settings can be associated with a particular drug. These delivery settings include temperature settings and delivery rate settings. The drug may be thermally altered at a fixed or variable rate and may reach one or more temperatures. For example, a phase transition compound/drug mixture may be heated from room temperature to 55 degrees Celsius over a 30 second period of time. The rate at which it is heated may be steady (more or less linear) or non-linear. Once the steady state temperature is reached, information about a delivery rate allows the controller 305 to operate actuator 515 to move plunger 415 at that rate. For example, it may be desirable to deliver the phase transition compound/drug mixture at a relatively fast rate (e.g. deliver the entire dosage in under one second) so that it forms a roughly spherical shaped bolus in the eye. Such a bolus can erode over time at a known rate to deliver the drug over an extended period of time. In other cases, plunger 415 may be actuated slowly so that the phase transition compound/drug mixture is delivered over a longer period of time (e.g. over several seconds). In such a case, the mixture cools as it enters the eye and forms a cylinder. This cylindrical shape provides more surface area and a higher release rate of the drug over time (i.e. the cylinder erodes faster than the sphere).

In other embodiments of the present invention, memory device 555 contains information about the characteristics of the tip segment. For example, information about the length and gauge of needle 210 may be stored on memory device 555. Information about the type of temperature control device (e.g. heater and its power or current draw) may also be stored on memory device 555. When delivering a drug into the eye, the length and gauge of needle 210 can be an important input to controller 305 so that the drug can be properly delivered. For example, a larger gauge or longer needle encloses more volume through which a drug must be expelled to reach the eye. The varying volumes of different needles may impact the amount of drug delivered. It may be necessary to compensate for different needle sizes by controlling the movement of plunger 415. For example, using a 25 or 27 gauge needle with a length of a few millimeters requires the plunger 415 to move a set distance to deliver a set quantity of drug. Using a 23 gauge needle with a length of a centimeter or more requires the plunger 415 to travel a different distance to deliver the same set quantity of drug. Likewise, the configuration of needle 210 may also impact the manner in which temperature control device 450 is operated. Using a longer or larger needle may require a phase transition substance to be heated slightly more than using a smaller or shorter needle.

In this manner, any of a number of different parameters may be stored on memory device 555. These parameters can be used by controller 305 to optimally control the system for a precise delivery of a drug into the eye. These parameters can also be used to implement safety features. For example, when the type of drug is stored on memory device 555, this information can be checked against an injection procedure. A checksum or CRC may also be included on memory device 555 to verify the accuracy or integrity of the data stored on it.

The parameters stored on memory device 555 can be used to operate the system to perform an optimal injection. In one method, a connection between a tip segment and a limited reuse assembly is recognized. One or more parameters are read from memory device 555. The injection is controlled based on the parameter. As previously noted, the parameters include, but are not limited to dosage information, delivery rate information, needle gauge, needle length, temperature control device information, drug information, thermal expansion information, and a checksum.

Figure 6:
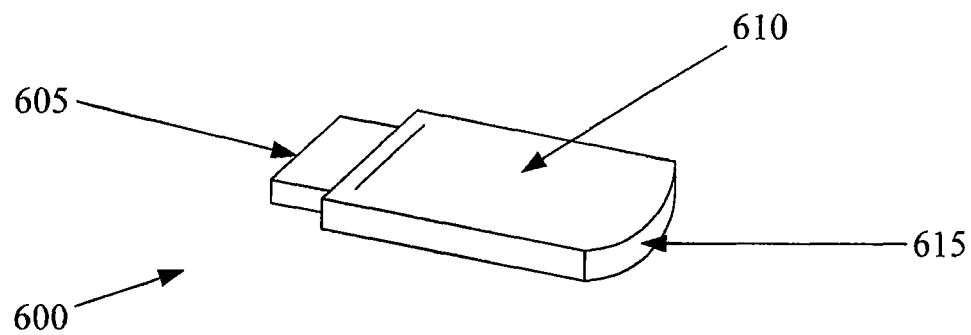
FIG. 6 is a perspective view of a dosage control card according to an embodiment of the present invention.

FIG. 6 is a perspective view of a dosage control card according to an embodiment of the present invention. In the embodiment of FIG. 6, dosage control device 600 is implemented in a memory card-type device. The same structure and functionality previously described with respect to memory assembly 555 of FIG. 5 is implemented in dosage control device 600. Dosage control device 600 contains a fuse, light, and memory device (not shown) as previously described. Dosage control device 600 has a connector end 605, a body 610, and a lighted end 615. In this embodiment, the connector end 605 is adapted to connect to and allow communication with a console box 700. A light 275 is incorporated in lighted end 615.

Figure 7:
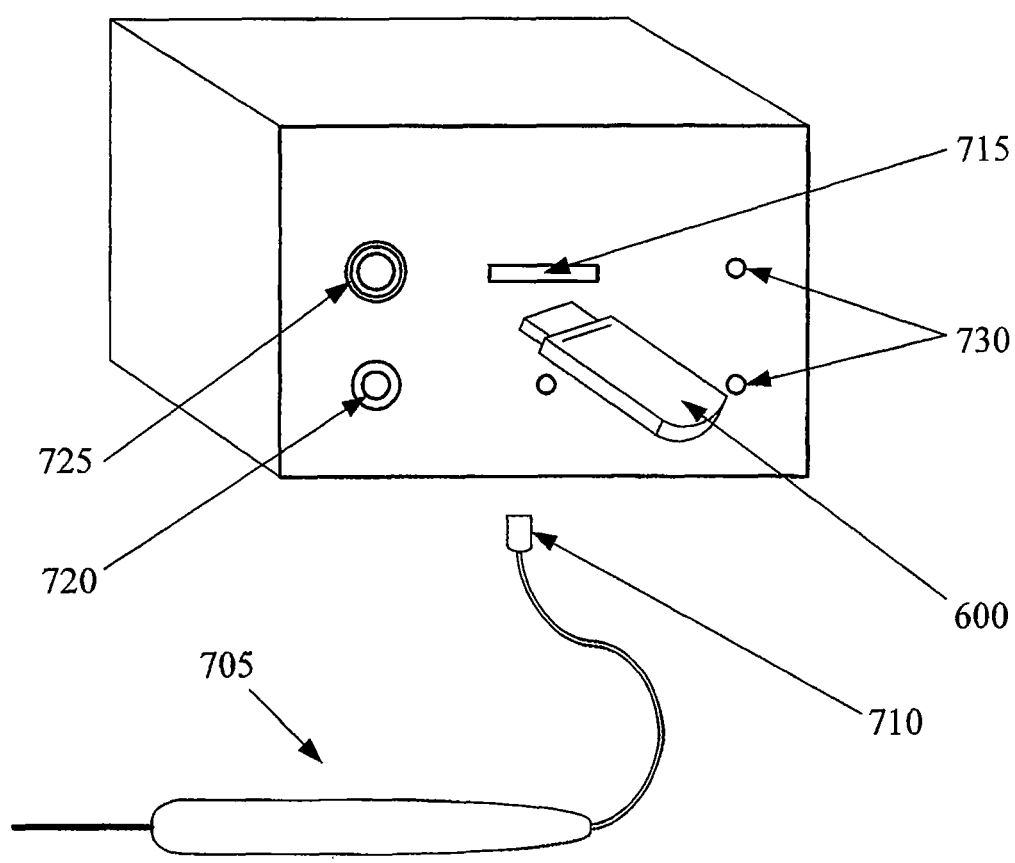
FIG. 7 is a perspective view of a console, a drug delivery device, and a dosage control card according to an embodiment of the present invention.

FIG. 7 is a perspective view of a console, a drug delivery device, and a dosage control card according to an embodiment of the present invention. In FIG. 7, console box 700 includes a slot 715, a port 720, a button 725, and indicators 730. Slot 715 is adapted to receive the connector end 605 of dosage control card 600. An injection device 705 has a connector 710. Port 720 is adapted to receive connector 710. Console box 700 includes a controller (not shown) that controls the operation of injection device 705. Injection device 705 includes the components of the embodiment shown in FIG. 5 with the exception of the power source, the controller, and possibly several indicators or lights. Those components are contained in the console box 700. In addition, the heater is optional, as it is optional in the previously described devices.

In operation, a medical professional removes injection device 705 and dosage control device 600 from sterilized packaging (not shown). The injection device 705 is connected to the console box 700 by connecting connector 710 to port 720. Dosage control device 600 is inserted into slot 715. The controller (not shown) in console box 700 reads the dosage information from the memory device on dosage control device 600. The controller in console box 700 then operates the injection device 705 to deliver the appropriate dosage in the manner previously described.

FIG. 8 is a circuit diagram of a hard wired memory circuit according to an embodiment of the present invention. In this embodiment, seven fuses (F1, F2, F3, F4, F5, F6, and F7), six resistors (R1, R2, R3, R4, R5, and R6), and one LED (L7) serve to store dosage data. The embodiment of FIG. 8 also includes six terminals (T1, T2, T3, T4, T5, and T6), a voltage line 810, and a ground line 820. Fuse F7 and LED L7 correspond to fuse 375 and optional light 275 in FIGS. 3 and 4.

The embodiment of FIG. 8 is capable of storing a five bit number and a checksum. As is commonly known, a voltage applied to voltage line 810 can be read across each of the six resistors. If the fuse in series with a particular resistor is blown, then no voltage will be read across that resistor. These two states (the presence or absence of a voltage across a resistor) correspond to a one or a zero in a binary number. In the embodiment of FIG. 8, five of the resistors contain dosage data. This dosage data is one of 32 distinct numbers. The sixth resistor holds checksum information.

For example, if fuses F2 and F3 are blown and fuses F1, F4, F5, and F6 are not blown, then no voltage (or a zero voltage) will be present across resistors R2 and R3 and a full voltage (+5 volts) will be present across resistors R1, R4, R5, and R6. In this example, the five bits correspond to the first five resistors (R1-R5), and the checksum corresponds to the sixth resistor (R6). The voltage across each resistor is read between the respective terminal (T1-T6) and the ground line 820. In this case, the five bit binary number is 10011 or 19, and the checksum is 1. The controller reads this number and the checksum, determines if the number is correct in light of the checksum, and then determines a dosage based on the number. In this case, the dosage control device defines 32 different dosage levels. The number 19 could correspond to a dosage of 48 microliters. In such a case, dosages from 10 to 72 microliters in two microliter increments can be defined by the dosage control device. The controller can then operate the plunger to deliver 48 microliters. After the dosage is delivered, a fuse can be blown, and the card can be rendered inoperable, as previously described.

From the above, it may be appreciated that the present invention provides an improved system for delivering precise volumes of a substance into an eye. The present invention provides a drug delivery device that is capable of delivering a precise dosage. The tip segment interfaces with a universal limited reuse hand piece assembly. Information on the dosage control device directs the injection device to deliver the proper dosage. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An injection device comprising:
    a dispensing chamber having an inner surface and an outer surface, the inner surface defining a cavity for receiving a quantity of a substance;
    a plunger engaged with the inner surface of the dispensing chamber, the plunger capable of sliding in the cavity of the dispensing chamber, the plunger fluidly sealed to the inner surface of the dispensing chamber;
    a controller for controlling the injection device;
    a temperature control device at least partially surrounding the dispensing chamber; and
    a memory device comprising a first fuse and a resistor, the memory device resistant to gamma sterilization techniques that would erase semiconductor memory, a parameter stored on the memory device;
    wherein the controller uses the parameter from the memory device to operate the injection device.

2. The injection device of claim 1 further comprising:
    a second fuse, such that after the substance has been delivered from the dispensing chamber, the second fuse is blown thus disabling the device.

3. The injection device of claim 1 further comprising:
    a needle fluidly coupled to the dispensing chamber.

4. The injection device of claim 2 further comprising a light in series with the second fuse.

5. The injection device of claim 1 further comprising:
    an actuator for driving the plunger.

6. The injection device of claim 1 wherein the parameter is an input to the controller to control the injection device to deliver the substance in a predefined manner.

* * * * *